United States Patent

Augart et al.

Patent Number: 6,054,482
Date of Patent: Apr. 25, 2000

[54] LACTAM-FREE AMINO ACIDS

[75] Inventors: Helmut Augart; Uwe Gebhardt, both of Waldkirch; Wolfgang Herrmann, Merzhausen, all of Germany

[73] Assignee: Gödecke Aktiengesellschaft, Berlin, Germany

[21] Appl. No.: 08/377,618

[22] Filed: Jan. 25, 1995

Related U.S. Application Data

[63] Continuation of application No. 08/020,270, Feb. 18, 1993, abandoned, which is a continuation of application No. 07/865,723, Apr. 8, 1992, abandoned, which is a continuation of application No. 07/570,500, Aug. 21, 1990, abandoned.

Foreign Application Priority Data

Aug. 25, 1989 [DE] Germany ............... 39 28 183

[51] Int. Cl.$^7$ .................................................. A01N 37/12
[52] U.S. Cl. ........................... 514/561; 562/504; 562/507
[58] Field of Search .................... 562/504, 507; 514/561

[56] References Cited

U.S. PATENT DOCUMENTS

| | | | |
|---|---|---|---|
| 4,024,175 | 5/1977 | Satzinger et al. | 260/514 |
| 4,087,544 | 5/1978 | Satzinger et al. | 424/305 |
| 4,152,326 | 5/1979 | Hartenstein et al. | 546/16 |
| 4,228,179 | 10/1980 | Hartenstein | 424/274 |
| 4,894,476 | 1/1990 | Butler et al. | 562/504 |

FOREIGN PATENT DOCUMENTS 2543821  4/1977  Germany.

OTHER PUBLICATIONS

Copending U.S. application 399056, filed Aug. 25, 1989.

Primary Examiner—Michael L. Shippen
Attorney, Agent, or Firm—Francis J. Tinney

[57] ABSTRACT

The present invention concerns cyclic amino acids of formula

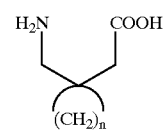

VII substantially free from the lactam

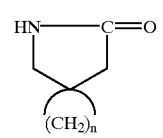

VIII wherein n is an integer of from 4 to 6, a process for the preparation thereof, compositions containing the compounds and methods of using them.

11 Claims, No Drawings

LACTAM-FREE AMINO ACIDS

This is a continuation of application Ser. No. 08/020,270, filed Feb. 18, 1993, now abandoned, which is a continuation of application Ser. No. 07/865,723, filed Apr. 8, 1992, now abandoned, is a continuation of application Ser. No. 07/570,500, filed Aug. 21, 1990, now abandoned.

BACKGROUND OF THE INVENTION

Gabapentin is a generic term used to identify the chemical compound (1-aminomethyl)-1-cyclohexaneacetic acid.

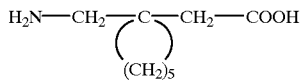

It is useful in therapy of certain cerebral disorders such as certain forms of epilepsy, faintness attacks, hypokinesis, and cranial traumas. U.S. Pat. Nos. 4,024,175 and 4,087,544 cover the compound and its uses. They also disclose an acid salt, i.e., gabapentin hydrochloride hydrate, in a ratio of 4:4:1 and a sodium salt of gabapentin hydrate in a ratio of 2:1.

U.S. Pat. No. 4,894,476 covers crystalline gabapentin monohydrate and methods for producing the same.

The patents describe various processes for the preparation of this and similar compounds of general formula

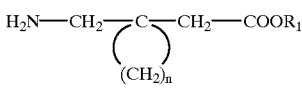

wherein $R_1$ is a hydrogen atom or a lower alkyl radical and n is 4, 5, or 6 and the pharmaceutically acceptable salts thereof, which depend upon known methods used for the preparation of primary amines or amino acid.

These patents are hereby incorporated by reference.

SUMMARY OF THE INVENTION

The instant invention covers a compound of formula

VII

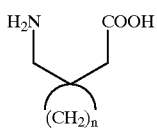

or a pharmaceutically acceptable salt thereof substantially free from

VIII

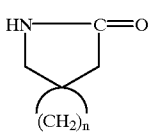

wherein n is an integer of from 4 to 6.

The preferred compound of formula VII is that where n is 5.

The instant invention also concerns a process for the purification of a compound of the instant invention comprising (a) treating a compound of formula VII substantially free from compound VIII with a semiconcentrated mineral acid, converting the lactam VIII into VII, (b) removing the anions of the mineral acid by ion exchange, leaving the purified VII, and (c) converting the product of step (b) to a pharmaceutically acceptable salt thereof, if desired.

A preferred process of the instant invention is one wherein the mineral acid hydrochloric acid is used and an ion exchanger is used for anion removal.

The instant invention further concerns pharmaceutical compositions which comprise a therapeutically effective amount of a compound according to claim 1 in combination with a pharmaceutically acceptable carrier.

The instant invention further concerns a method for treating epilepsy in a mammal in need of such treatment which comprises administering an antiepileptically effective amount of a compound of claim 1 to a mammal in need thereof.

DETAILED DESCRIPTION OF THE INVENTION

The present invention is concerned with lactam-free cyclic amino acids, a process for the preparation thereof and pharmaceutical compositions containing them.

German Patent 24 60 891 concerns known cyclic amino acid derivatives of the general formula I (I)

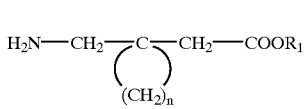

wherein $R_1$ is a hydrogen atom or lower alkyl and n is an integer 4, 5 or 6, as well as the pharmacologically acceptable salts thereof. These compounds possess valuable pharmacodynamic properties. The compounds of formula (I) have an extraordinarily low toxicity. In animal experiments, a remarkable protective effect was found against cramp induced by thiosemicarbazide and against cardiazole cramp. The compounds can be used for the therapy of certain cerebral diseases. They can be used in the treatment of certain forms of epilepsy, of attacks of dizziness, of hypokinesis and of cranial trauma and the improvement of the cerebral function. Therefore, they are especially effective for the treatment of geriatric conditions. The compounds of formula (I) can be prepared in known manner either by a) converting a compound of the formula II (II)

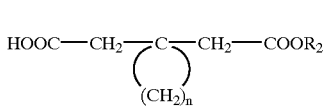

wherein $R_2$ is an alkyl radical containing up to 8 carbon atoms and n has the same meaning as above, via a reactive acid derivative into an azide which is then subjected to a Curtius reaction; or b) subjecting a compound of the formula III

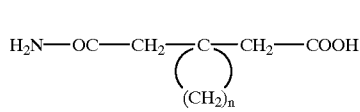

wherein n has the same meaning as above, to a Hofmann reaction; or c) subjecting a compound of the general formula IV

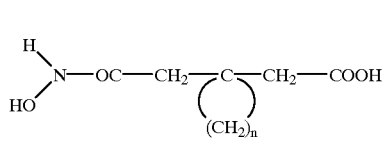

wherein n has the same meaning as above, to a Lossen rearrangement; whereafter, if desired, the free amino acid obtained is converted by esterification into a lower alkyl ester or by reaction with an acid or base into a pharmacologically acceptable salt.

Aminomethyl-1-cyclohexaneacetic acid (gabapentin) of the formula Va

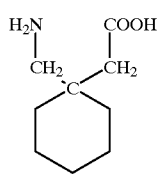

has proved to be especially potent. Gabapentin displays a certain structural relationship to gamma-aminobutyric acid (GABA) which is not able to pass the blood-brain barrier. Gabapentin does not possess this disadvantage and thus represents a very effective anticonvulsive with an extraordinarily low toxicity (Drugs of the Future. 11/6, 518–519/ 1986).

The preparation and storage of compounds of formula (I) in which $R_1$ is hydrogen present problems. These problems have been partly overcome and they still are a problem in the development of usable forms of administration. The compounds obtained showed considerable variations in the degree of purity, without apparent reason. By means of special, additional purification steps, it first appeared that this problem could be overcome. Long-term storage stability of even very pure compounds (I) displayed greatly differing stabilities with progressively long storage times. It was difficult to determine the cause for the deficient stability since this clearly depended upon initially unknown conditions. A long series of systematic investigations led to a solution of the problem of making available stable active materials and forms of composition of the compounds (I).

The hydrochloride of gabapentin was the most suitable form of the active material since salts and especially hydrochlorides as a rule usually provide especially good stability and good solubility. However, in some cases, pharmaceutical compositions were even more unstable than the free amino acid.

According to the reaction sequence:

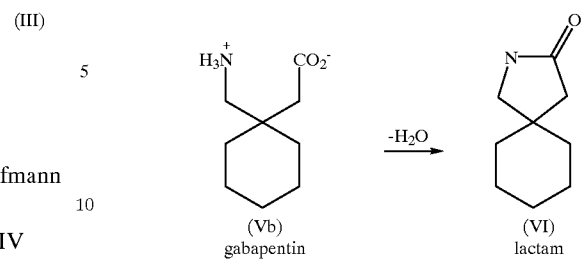

gabapentin forms, in a manner analogous to the other compounds of the formula VII,

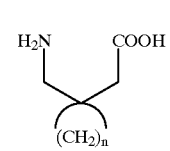

wherein n is 4, 5, or 6 and preferably 5, the lactam (VI). However, lactams of the formula VIII

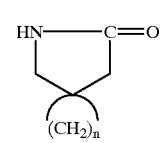

in which n has the same meaning as above, are formed not only in the course of the preparation but, surprisingly, also in the case of storage.

This unexpected reaction in the solid phase and under dry storage conditions led, because of the water liberated in the case of the cyclization, to additional problems for the stability of dry medicinal forms, for example, tablets and capsules, which, in the presence of moisture, tend to stick or to soften.

Attempts to keep the lactam content of the active material used as low as possible from the very beginning led, in the case of the preparation as well as in the case of storage of the active substance, not only in pure form but also in final preparations, to further initially unsolvable problems because it was found that the cyclization reaction surprisingly also took place in the alkaline region.

The lactams display a certain toxicity and must, therefore, be avoided as far as possible. For example, gabapentin has a toxicity ($LD_{50}$, mouse) of more than 8000 mg/kg, for the corresponding lactam (VI) a toxicity of 300 mg/kg. Consequently, these impurities and the potential formation of such decomposition products during storage of pharmaceutical compositions must be reduced to a minimum for reasons of safety.

Finally, in the case of investigations of final pharmaceutical forms, it was found, as a further problem, that the cause of the lactam formation was apparently also the catalytic effects of adjuvant materials which also did not follow any recognizable logic. In order to establish which adjuvant materials promote the lactam formation, laborious serial investigations had, therefore, to be carried out. These showed, for example, that Poloxamer NF behaved completely neutral and, in the case of the sole presence thereof, did not impair the stability of the active material gabapentin, whereas in the case of the use of polyethylene glycol (PEG), cyclization to the lactam took place to a considerable extent. In another test series with very pure active substance, PEG was found to be indeed usable as an excipient.

The following adjuvant materials, for example, reduced the stability of the compounds (I) and should be avoided in the preparation of pharmaceutical compositions: modified maize starch, sodium croscarmelose, glycerol behenic acid ester, methacrylic acid co-polymers (types A and C), anion exchangers titanium dioxide, and silica gels such as Aerosil 200.

On the other hand, the following adjuvant materials had no noticeable influence on the stability of the compounds (I): hydroxypropylmethylcellulose, polyvinylpyrrolidone, crospovidon, poloxamer 407, poloxamer 188, sodium starch glycolate, copolyvidone, maize starch, cyclodextrin, lactose, talc, as well as co-polymers of dimethylamino-methacrylic acid and neutral methacrylic acid ester.

In order not to exceed the upper limit of 0.5% by weight of gabapentin lactam (referred to the gabapentin), which is regarded as being permissible, and in order to ensure the storage stability not only of the active material but also of the corresponding pharmaceutical forms of preparation, the following procedures are to be maintained:

1. The active materials of formula (I) must be prepared as highly purified, nonderivatized free amino acids, for example, from the corresponding hydrochloride by ion exchange. The proportion of remaining hydrochloride admixtures should thereby not exceed 20 ppm. The same also applies to other mineral acids.
2. In the case of pharmaceutical preparations or compositions, by the precise choice of adjuvant materials, every catalysis of the lactam formation must be suppressed.
3. By controls, it must be ensured that the above conditions are fulfilled. As a rule, this is the case when the lactam formation, under the storage conditions generally applicable for medicaments, does not increase within a period of time of 1 year after production of the pharmaceutical compositions or of the active material by more than 0.2% by weight and preferably 0.1% by weight, referred to the pure active material.

Therefore, according to the present invention, cyclic amino acids of the formula VII

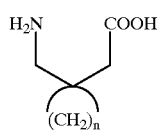

(VII)

wherein n is 4, 5, or 6 and preferably 5, and pharmaceutical compositions containing them, have a content of lactam of the formula VIII

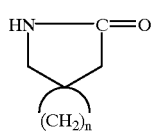

(VIII)

wherein n has the same meaning as above, of less than 0.5% by weight.

Furthermore, the present invention provides cyclic amino acids of formula (VII) and pharmaceutical compositions containing at least one compound of formula (VII) which satisfies the above-mentioned criteria, wherein the content of lactam of formula (VIII) at 25° C. and an atmospheric humidity of 50% does not increase during the course of 1 year after preparation by more than 0.2% by weight (referring to the active material).

The following examples are given for the purpose of illustrating the present invention and are not intended to limit the scope in any way.

EXAMPLE 1

1-(Aminomethyl)-cyclohexaneacetic acid hydrochloride 22.3 L of water and 22.3 L of concentrated hydrochloric acid are mixed in a T100 reactor and 6.41 kg gabapentin lactam added while stirring. The clear brown solution formed is subsequently boiled under reflux at 108° C. for 6 hours. The reaction mixture is then left until it has cooled to 28° C. The white precipitate obtained is again dissolved by the addition of a further 40 L of water. For the removal of still undissolved lactam, the reaction mixture is extracted three times with, in each case, 30 L of dichloromethane. The pale yellow aqueous phase is evaporated to dryness in a vacuum evaporator (QVF 100L). At 133 Pa, the temperature finally reached 80° C. The almost dry crystal mass is stirred up with 12.8 L of acetone and sucked off. It is then washed with 2 L of acetone and dried for 4 hours at 60° C. The yield is about 60% of theory.

EXAMPLE 2

1-(Aminomethyl)-cyclohexaneacetic acid

A 3 m long and 200 mm wide chromatography column is filled with 50 L of ion exchanger resin (IRA 68). The resin is regenerated with a solution of 14 L of concentrated aqueous ammonia in 300 L of demineralized water and subsequently washed with 150 L of demineralized water. As soon as the eluate has reached a pH of 6.8 and chloride can no longer be detected, a solution of 8.67 kg (40.8 mole) 1-aminomethyl-1-cyclohexaneacetic acid hydrochloride in 43 L of demineralized water is applied to the column. The free amino acid is eluted with demineralized water at a rate of 1.5 L/min and collected in 15 fractions each of 15 L. The combined fractions are evaporated at 6.65 KPa and at most 45° C. The white solid residue is introduced into 20 L of methanol, heated to reflux, filtered, and cooled to −10° C. The product which crystallizes out is centrifuged, washed with 10 L of cold methanol, and dried for 17 hours at 30° to 40° C. 4.9 kg (71% of theory) of pure 1-(aminomethyl)-cyclohexaneacetic acid are obtained; m.p. 165° C. A further 0.8 kg can be obtained by working up the mother liquors.

We claim:

1. A process for the preparation of a compound of Formula VII

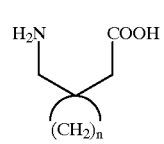

VII wherein n is an integer of from 5 containing less than 0.5% by weight of a compound of Formula VIII

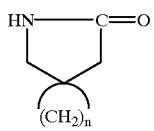

(VIII)

wherein n is as defined above and less than 20 ppm of an anion of a mineral acid comprising:
(a) hydrolysis of a compound of Formula VII containing a compound of Formula VIII or of a compound of Formula VIII alone with a mixture of equal volumes of a concentrated mineral acid and water to afford an acid addition salt of a compound of Formula VII and
(b) converting the acid addition salt of a compound of Formula VII by ion exchange to a compound of Formula VII containing less than 0.5% by weight of a compound of Formula VIII and less than 20 ppm of an anion of a mineral acid.

2. A process according to claim 1, wherein in step (a) the acid is hydrochloric acid.

3. A process for preparing stable and pure pharmaceutical compositions containing a compound of formula (VII)

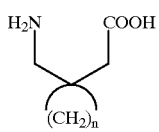

(VII)

wherein n is an integer of 5 and pharmaceutically acceptable adjuvants consisting of the steps of
(a) hydrolysis of a compound of formula VII

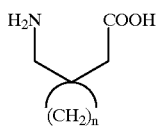

(VII)

wherein n is as defined above containing a compound of formula VIII

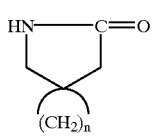

(VIII)

wherein n is as defined above or a compound of Formula VIII alone with a mixture of equal volumes of a concentrated mineral acid and water to afford an acid addition salt of a compound of formula VII substantially free of a compound of formula VIII, (b) converting the acid addition salt of a compound of formula VII by ion exchange to a compound of formula VII containing less than 0.5% by weight of a compound of formula VIII, wherein the proportion of remaining anion of a mineral acid does not exceed 20 ppm,
(c) adding pharmaceutically acceptable adjuvants to form a pharmaceutical composition wherein the adjuvants do not promote the formation of a lactam of formula VIII ensuring that the lactam formation under the storage conditions at 25° C. and an atmospheric humidity of 50% does not increase within a period of time of one year after the production of the pharmaceutical compositions or of the active material by more than 0.2% by weight, referred to the pure active material.

4. A process of claim 3, wherein the pharmaceutically acceptable adjuvants are selected from the group consisting of hydroxypropylmethylcellulose, polyvinylpyrrolidone, crospovidone, poloxamer 407, poloxamer 188, sodium starch glycolate, copolyvidone, maize starch, cyclodextrine, lactose, talc and copolymers of dimethylamino-methacrylic acid and neutral methacrylic acid ester.

5. A process of claim 3, wherein the mineral acid is hydrochloric acid.

6. A process of claim 4, wherein the mineral acid is hydrocholoric acid.

7. A stable and pure pharmaceutical composition in unit dry medicinal dosage form consisting essentially of:
(i) an active ingredient which is gabapentin in the free amino acid, crystalline anhydrous form containing less than 0.5% by weight of its corresponding lactam and less than 20 ppm of an anion of a mineral acid and
(ii) one or more pharmaceutically acceptable adjuvants that do not promote conversion of more than 0.2% by weight of the gabapentin to its corresponding lactam form when stored at 25° C. and an atmospheric humidity of 50% for one year.

8. A pharmaceutical composition according to claim 7, in which the pharmaceutically acceptable aadjuvant is selected from the group consisting of hydroxypropyl-methylcellulose, polyvinylpyrrolidone, crospovidon, poloxamer 407, poloxamer 188, sodium starch glycolate, copolyvidone, maize starch, cyclodextrin, lactose, talc, co-polymers of dimethylamino-methacrylic acid and neutral methacrylic acid ester.

9. A pharmaceutical composition according to claim 7, wherein the dry medicinal dosage form is a tablet.

10. A pharmaceutical composition according to claim 7, wherein the dry medicinal dosage form is a capsule.

11. A pharmaceutical composition according to claim 7,wherein in (i) the mineral acid is hydrochloric acid.

* * * * *

UNITED STATES PATENT AND TRADEMARK OFFICE
CERTIFICATE OF CORRECTION

PATENT NO. : 6,054,482
DATED : April 25, 2000
INVENTOR(S) : Helmut Augart, Uwe Gebhardt, and Wolfgang Herrmann Page 1 of 1

It is certified that error appears in the above-identified patent and that said Letters Patent is hereby corrected as shown below:

Title Page

Item: [56] Insert: -- Handbook of Pharmaceutical Excipients", Ed. Wade and Weller, American Pharmaceutical Association, Washington, D.C., pp. 519-521 (1994) --;

Column 6
Line 66, "from 5" should read -- 5 --; and

Column 8
Line 5, "20 ppm," should read -- 20 ppm, and --.

Signed and Sealed this

Twenty-first Day of August, 2001

Attest:

*Nicholas P. Godici*

NICHOLAS P. GODICI
*Attesting Officer*   *Acting Director of the United States Patent and Trademark Office*